(12) United States Patent
Parthasaradhi Reddy et al.

(10) Patent No.: US 8,536,151 B2
(45) Date of Patent: Sep. 17, 2013

(54) PROCESS FOR PREPARING LAMIVUDINE POLYMORPH FORM

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Kesireddy Subash Chander Reddy, Hyderabad (IN)

(73) Assignee: Hetero Research Foundation (IN)

( * ) Notice: Subject to any disclaimer, the term of this patent is extended or adjusted under 35 U.S.C. 154(b) by 80 days.

(21) Appl. No.: 12/742,743

(22) PCT Filed: Sep. 1, 2008

(86) PCT No.: PCT/IN2008/000556
§ 371 (c)(1),
(2), (4) Date: May 13, 2010

(87) PCT Pub. No.: WO2010/023676
PCT Pub. Date: Mar. 4, 2010

(65) Prior Publication Data
US 2011/0137034 A1    Jun. 9, 2011

(51) Int. Cl.
*A61K 31/70*     (2006.01)
*A61K 31/505*    (2006.01)
*A61K 31/52*     (2006.01)
*A61K 31/675*    (2006.01)
*C07D 239/20*    (2006.01)

(52) U.S. Cl.
USPC ......................................................... 514/50

(58) Field of Classification Search
USPC ......................................................... 544/317
See application file for complete search history.

(56) References Cited

U.S. PATENT DOCUMENTS

| 5,905,082 A | 5/1999 | Roberts et al. |
| 2012/0077772 A1 * | 3/2012 | Parthasaradhi Reddy et al. ............... 514/50 |

FOREIGN PATENT DOCUMENTS

| WO | 9117159 A1 | 11/1991 |
| WO | 92/21676 A1 | 12/1992 |
| WO | 03027106 A1 | 4/2003 |
| WO | 2007119248 A1 | 10/2007 |
| WO | 2010023676 A2 | 3/2010 |

OTHER PUBLICATIONS

Harris et al., 'Polymorphism' in a novel anti-viral agent: Lamivudine, Journal of the Chemical Society, Perkin Transaction 2, 1997, pp. 2653-2659.
International Search Report for PCT/IN2008/000556 dated Sep. 1, 2008 and Written Opinion.

* cited by examiner

*Primary Examiner* — James O Wilson
*Assistant Examiner* — Ebenezer O Sackey
(74) *Attorney, Agent, or Firm* — Cantor Colburn LLP

(57) ABSTRACT

The invention relates to a process for the preparation of stable lamivudine polymorph form and to a composition comprising thereof.

8 Claims, 1 Drawing Sheet

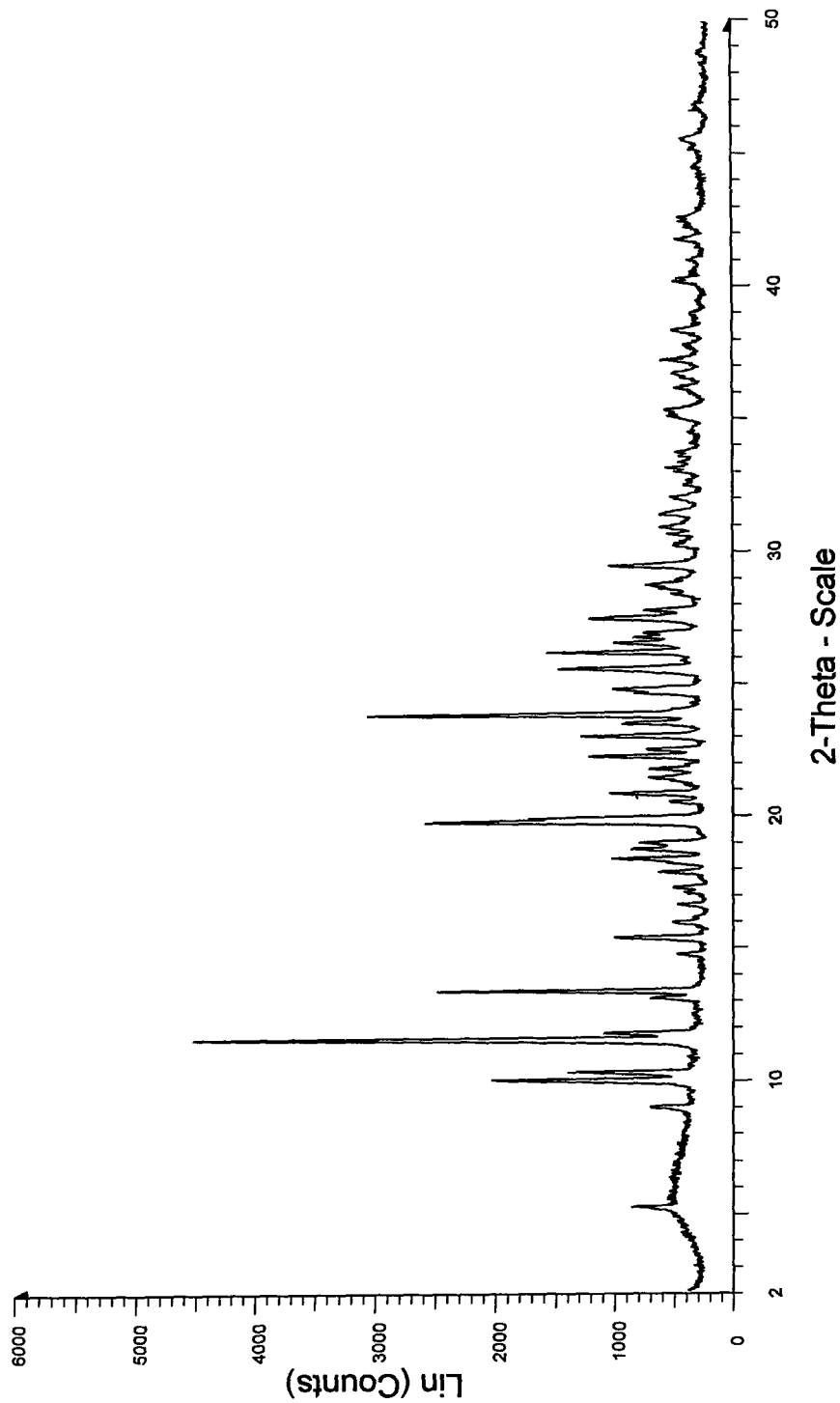

PROCESS FOR PREPARING LAMIVUDINE POLYMORPH FORM

FIELD OF THE INVENTION

The invention relates to a process for the preparation of stable lamivudine polymorph form and to a composition comprising thereof.

BACKGROUND OF THE INVENTION

Lamivudine is known by the chemical name (2R-cis)-4-Amino-1-[2-(hydroxymethyl)-1,3-oxathiolan-5-yl]-2(1H)-pyrimidinone. Lamivudine is represented by the following structure.

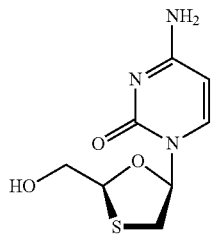

Lamivudine is a reverse transcriptase inhibitor used in the treatment of HIV infection alone or in combination with other class of Anti HIV drugs.

Lamivudine may be prepared using the procedures described in WO 91/17159.

It has been reported in literature [J. Pharm. Sci., 1996, 85, 193-199; U.S. Pat. No. 5,905,082] that lamivudine exists in two polymorphs known as polymorphic Form I and Form II. Form I of lamivudine is a needle shaped crystals. Form II of lamivudine is a bipyramidyl crystals. Lamivudine in the form of bipyramidyl crystals has a melting point of 177-178° C. and a melting point of 124-127° C. when in the form of needle shaped crystals.

WO 03027106 A1 discloses a process for the preparation of lamivudine polymorph Form II. However, lamivudine in this form I is not suitable for pharmaceutical formulations in the form of solid dosage forms because of their physical properties, such as poor flow characteristics. Form I crystals are a less stable polymorphic form and certain pharmaceutical unit operations such as milling may cause conversion of form I to form II which is an undesirable characteristic for manufacture of solid dosage forms.

WO 2007/119248 discloses crystalline hemihydrate (Form III) of lamivudine. Crystalline form I have inferior flow property and also lower bulk density, which create problem in handling the product during formulation.

It has been found that lamivudine polymorphs form I which is stable during pharmaceutical operations such as milling, can be prepared by following certain specific procedure.

Thus, the object of the invention is to prepare stable lamivudine polymorph form I suitable for pharmaceutical preparation.

DETAILED DESCRIPTION OF THE INVENTION

In accordance with the present invention, there is provided a process for the preparation of lamivudine polymorph form I.

In accordance with one aspect of the present invention, a process is provided for preparation of lamivudine polymorph form I, which comprises:
a) dissolving lamivudine in alcohol;
b) refluxing for about 30 minutes to 45 minutes;
c) cooling to about 0° C. to 10° C.;
d) maintaining for about 1 hour to 1 hour 30 minutes at about 0° C. to 10° C.;
e) filtering the solid separated and washing with alcohol;
f) drying the material at 60° C. to 70° C.;
g) dissolving the solid obtained in a mixture of an alcohol and a water;
h) heating to 40° C. to 45° C. for about 30 minutes to 45 minutes;
i) cooling to about 25° C. to 35° C.;
j) maintaining for about 1 hour 30 minutes to 2 hours at about 25° C. to 35° C.; and
k) filtering the solid separated and drying the material at 45° C. to 50° C.

Wherein the alcohol is selected from methanol, ethanol, isopropyl alcohol, tert-butyl alcohol and n-butyl alcohol; or mixture thereof. Preferred solvent is methanol or ethanol.

Lamivudine used in step (a) may be in any polymorph. Typically polymorph form I prepared according to the present invention has the water content of 2% or below as determined by Karl Fischer (KF) method.

In accordance with another aspect of the present invention a solid pharmaceutical composition comprising lamivudine polymorph Form I prepared according to the present invention.

BRIEF DESCRIPTION OF THE DRAWING

FIG. 1 is X-ray powder diffraction spectrum of lamivudine polymorph form I.

X-ray powder diffraction spectrum was measured on a bruker axs D8 advance X-ray powder diffractometer having a copper-Kα radiation. Approximately 1 gm of sample was gently flattered on a sample holder and scanned from 2 to 50 degrees two-theta, at 0.03 degrees to theta per step and a step of 0.5 seconds. The sample was simply placed on the sample holder. The sample was rotated at 30 rpm at a voltage 40 KV and current 35 mA.

The invention will now be further described by the following examples, which are illustrative rather than limiting.

EXAMPLES

Example 1

Lamivudine (35 gm) is dissolved in methanol (350 ml) and activated carbon (1 gm) is added to the solution. Then the contents are heated to reflux and maintained for 40 minutes. The mass was further cooled to 5° C. during a period of 1 hour 15 minutes. Then the separated solid is filtered, washed with methanol (40 ml) and dried at 60-70° C. for 4 hours. The obtained solid is dissolved in a mixture of (3:1) water and ethanol (75 ml). Then the contents are heated to 45° C. and stirred for 40 minutes to give clear solution. The solution was cooled to 30° C. in 1 hour 45 minutes. The mass was then cooled to 5° C. Then product was filtered and dried at 45-50° C. for 4 hours to give 26 gm of Lamivudine polymorph Form I.

Pharmaceutical Formulations

A compositions comprising Lamivudine polymorph Form I were prepared according to the present invention shown below in example 2-6:

Example 2

Lamivudine 150 mg tablets.
The components and their amounts were as follows:

| Component | Weight (mg)/Tablet |
| --- | --- |
| Lamivudine | 150 |
| Microcrystalline cellulose | 106 |
| Sodium starch glycolate | 17 |
| Magnesium stearate | 7 |
| Core tablet weight | 280 |
| Opadry white ys-1-7003 | 7 |
| Coated tablet weight | 287 |

Example 3

Lamivudine 300 mg tablets.
The components and their amounts were as follows:

| Component | Weight (mg)/Tablet |
| --- | --- |
| Lamivudine | 300 |
| Microcrystalline cellulose | 212 |
| Sodium starch glycolate | 34 |
| Magnesium stearate | 14 |
| Core tablet weight | 560 |
| Opadry white ys-1-7003 | 14 |
| Coated tablet weight | 574 |

Example 4

Lamivudine 100 mg tablets.
The components and their amounts were as follows:

| Component | Weight (mg)/Tablet |
| --- | --- |
| Lamivudine | 100 |
| Microcrystalline cellulose | 153 |
| Sodium starch glycolate | 20 |
| Magnesium stearate | 7 |
| Core tablet weight | 280 |
| Opadry pink 03A84598 | 7 |
| Coated tablet weight | 287 |

Example 5

Lamivudine 150 mg tablets.
The components and their amounts were as follows:

| Component | Weight (mg)/Tablet |
| --- | --- |
| Lamivudine | 150 |
| Lactose monohydrate | 85 |
| Microcrystalline cellulose | 21 |
| Croscarmellose sodium | 17 |
| Magnesium stearate | 7 |
| Core tablet weight | 280 |
| Opadry white ys-1-7003 | 7 |
| Coated tablet weight | 287 |

Example 6

Lamivudine 300 mg tablets.
The components and their amounts were as follows:

| Component | Weight (mg)/Tablet |
| --- | --- |
| Lamivudine | 300 |
| Lactose monohydrate | 170 |
| Microcrystalline cellulose | 42 |
| crospovidone | 34 |
| Magnesium stearate | 14 |
| Core tablet weight | 560 |
| Opadry white ys-1-7003 | 14 |
| Coated tablet weight | 574 |

The compositions of shown in examples 2-6 were prepared by the process described below:

Lamivudine polymorph Form I was blended with additives like microcrystalline cellulose and/or lactose monohydrate, sodium starch glycolate or croscarmellose sodium or crospovidone and magnesium stearate in a blender and milling for 5 to 10 minutes.

Analysis of the compositions of examples 2-6 prepared by the process described above showed that Lamivudine polymorph Form I used as active ingredients does not have the tendency to transform into a different polymorph form.

We claim:

1. A process for preparation of lamivudine polymorph form I, which comprises:
   a) dissolving lamivudine in alcohol;
   b) refluxing for about 30 minutes to 45 minutes;
   c) cooling to about 0° C. to 10° C.;
   d) maintaining for about 1 hour to 1 hour 30 minutes at about 0° C. to 10° C.;
   e) filtering the solid separated and washing with alcohol;
   f) drying the material at 60° C. to 70° C. ;
   g) dissolving the solid obtained in a mixture of an alcohol and a water;
   h) heating to 40° C. to 45° C. for about 30 minutes to 45 minutes;
   i) cooling to about 25° C. to 35° C.;
   j) maintaining for about 1 hour 30 minutes to 2 hours at about 25° C. to 35° C.; and
   k) filtering the solid separated and drying the material at 45° C. to 50° C. to form lamivudine polymorph form I, wherein the alcohol is selected from methanol, ethanol, isopropyl alcohol, tertbutyl alcohol and n-butyl alcohol; or mixture thereof.

2. The process according to claim 1, wherein the alcohol is methanol or ethanol.

3. The processing according to claim 2, wherein the alcohol used in step (a) and step (e) is methanol.

4. The process according to claim 2, wherein the alcohol used in step (g) is ethanol.

5. A solid pharmaceutical dosage form comprising lamivudine polymorph form I prepared according to the process of claim 1.

6. The solid pharmaceutical composition of claim 5, wherein the solid pharmaceutical dosage form is a tablet or capsule.

7. The process according to claim 1, further comprising preparing a solid pharmaceutical dosage form comprising the lamivudine polymorph form I.

8. The process according to claim 7, wherein the solid pharmaceutical dosage form is a tablet or capsule.

\* \* \* \* \*